US008909322B2

(12) United States Patent
Anderson et al.

(10) Patent No.: US 8,909,322 B2
(45) Date of Patent: Dec. 9, 2014

(54) CATHETER FOR MAGNETIC RESONANCE GUIDED PROCEDURES

(75) Inventors: Kevan Anderson, Oshawa (CA); Graham Wright, Toronto (CA)

(73) Assignee: Sunnybrook Health Sciences Centre, Toronto, Ontario (CA)

( * ) Notice: Subject to any disclaimer, the term of this patent is extended or adjusted under 35 U.S.C. 154(b) by 544 days.

(21) Appl. No.: 12/557,840

(22) Filed: Sep. 11, 2009

(65) Prior Publication Data

US 2010/0063383 A1  Mar. 11, 2010

Related U.S. Application Data

(60) Provisional application No. 61/095,974, filed on Sep. 11, 2008.

(51) Int. Cl.
*A61B 5/00* (2006.01)
*A61M 25/01* (2006.01)
*G01R 33/28* (2006.01)
*G01R 33/34* (2006.01)

(52) U.S. Cl.
CPC .......... *A61M 25/01* (2013.01); *G01R 33/34084* (2013.01); *A61M 2205/3515* (2013.01); *A61M 25/0127* (2013.01); *A61M 2025/0166* (2013.01); *G01R 33/288* (2013.01); *G01R 33/287* (2013.01)
USPC .......................................... 600/424; 600/423

(58) Field of Classification Search
USPC .......................... 600/409, 411, 423, 424, 431; 604/93.01; 324/318, 322
See application file for complete search history.

(56) References Cited

U.S. PATENT DOCUMENTS

| 5,728,079 | A | 3/1998 | Weber et al. |
| 6,019,737 | A | 2/2000 | Murata |
| 6,171,240 | B1 | 1/2001 | Young et al. |
| 6,263,229 | B1 | 7/2001 | Atalar et al. |
| 6,317,091 | B1 * | 11/2001 | Oppelt .......................... 324/318 |
| 6,458,088 | B1 | 10/2002 | Hurtak et al. |
| 6,606,513 | B2 | 8/2003 | Lardo et al. |
| 6,628,980 | B2 * | 9/2003 | Atalar et al. .................. 600/423 |
| 6,675,033 | B1 | 1/2004 | Lardo et al. |
| 6,701,176 | B1 | 3/2004 | Halperin et al. |

(Continued)

FOREIGN PATENT DOCUMENTS

| CA | 2349235 A1 | 11/2000 |
| CA | 2398967 A1 | 9/2001 |
| WO | 0173461 A2 | 10/2001 |
| WO | 2007064739 A2 | 6/2007 |

OTHER PUBLICATIONS

Karmarkar et al. MR-Trackable Intramyocardial Injection Catheter. Magn Reson Med. Jun. 2004;51(6):1163-72.*

(Continued)

*Primary Examiner* — Unsu Jung
*Assistant Examiner* — Phong K Huynh
(74) *Attorney, Agent, or Firm* — Norton Rose Fulbright Canada LLP

(57) ABSTRACT

A catheter for magnetic resonance (MR) guided procedures comprising: a catheter body having a lumen for accommodating an intravascular device; a magnetic coupling component in the catheter body, the magnetic coupling component being designed to magnetically couple with a conductive length on the intravascular device, the magnetic coupling resulting in a signal; the catheter having a connection to deliver the signal to a processor.

42 Claims, 13 Drawing Sheets

(56) References Cited

U.S. PATENT DOCUMENTS

| | | | |
|---|---|---|---|
| 6,766,185 B2 | 7/2004 | Scott | |
| 6,799,067 B2 | 9/2004 | Pacetti et al. | |
| 6,845,259 B2 | 1/2005 | Pacetti et al. | |
| 7,027,854 B2 | 4/2006 | Fuderer et al. | |
| 7,096,057 B2 | 8/2006 | Hockett et al. | |
| 7,155,271 B2 | 12/2006 | Halperin et al. | |
| 2001/0011889 A1* | 8/2001 | Golan | 324/318 |
| 2003/0028094 A1* | 2/2003 | Kumar et al. | 600/423 |
| 2003/0208142 A1 | 11/2003 | Boudewijn et al. | |
| 2004/0097804 A1 | 5/2004 | Sobe | |
| 2004/0220470 A1* | 11/2004 | Karmarkar et al. | 600/423 |
| 2006/0106303 A1 | 5/2006 | Karmarkar et al. | |
| 2006/0184011 A1 | 8/2006 | Macaulay et al. | |

OTHER PUBLICATIONS

Dick et al. Invasive human magnetic resonance imaging: feasibility during revascularization in a combined XMR suite. Catheter Cardiovasc Interv. Mar. 2005;64(3):265-74.*

Kuehne et al. "Catheter Visualization with Resonant Markers at MR Imaging-guided Deployment of Endovascular Stents in Swine". Radiology 2004; 233:774-780.*

Wong et al. "An Optical System for Wireless Detuning of Parallel Resonant Circuits". Journal of Magnetic Resonance Imaging 12:632-638 (2000).*

European Patent Office, "Extended European Search Report" for corresponding EP Application No. 09812591.7 dated Sep. 23, 2011, Germany.

Weiss, Steffen et al., "In Vivo Safe Catheter Visualization and Slice Tracking Using an Optically Detunable Resonant Marker", Magnetic Resonance in Medicine Journal, 2004, pp. 860 to 868, vol. 52.

Omary, Reed A. et al., "Real-Time MR Imaging-Guided Passive Catheter Tracking with Use of Gadolinium-Filled Catheters", JVIR Journal, Sep. 2000, pp. 1079 to 1085, vol. 11, No. 8.

Miquel, Marc E. et al., "Visualization and Tracking of an Inflatable Balloon Catheter Using SSFP in a Flow Phantom and in the Heart and Great Vessels of Patients", Magnetic Resonance in Medicine Journal, 2004, pp. 988 to 995, vol. 51.

Kozerke, Sebastian et al., "Catheter Tracking and Visualization Using 19F Nuclear Magnetic Resonance", Magnetic Resonance in Medicine Journal, 2004, pp. 693 to 697, vol. 52.

Dumoulin, C.L. et al., "Real-Time Position Monitoring of Invasive Devices Using Magnetic Resonance", Journal, unknown date, pp. 411 to 415.

Hillenbrand, Claudia M. et al., "Active Device Tracking and High-Resolution Intravascular MRI Using a Novel Catheter-Based, Opposed-Solenoid Phased Array Coil", Magnetic Resonance in Medicine Journal, 2004, pp. 668 to 675, vol. 51.

Ocali, Ogan et al., "Intravascular Magnetic Resonance Imaging Using a Loopless Catheter Antenna", Journal, unknown date, pp. 112 to 118.

Liu, Chia-Ying et al., "Safety of MRI-Guided Endovascular Guidewire Applications", Journal of Magnetic Resonance Imaging, 2000, pp. 75 to 78.

Nitz, Wolfgang R. et al., "On the Heating of Linear Conductive Structures as Guide Wires and Catheters in Interventional MRI", Journal of Magnetic Resonance Imaging, 2001, pp. 105 to 114.

Yeung, Christopher J. et al., "A Green's Function Approach to Local RF Heating in Interventional MRI", Journal, May 2001, pp. 826 to 832.

Yeung, Christopher J. et al., "RF Transmit Power Limit for the Barewire Loopless Catheter Antenna", Journal of Magnetic Resonance Imaging, 2000, pp. 86 to 91.

Kreger, S. et al., "Evaluation of an MR-Compatible Guidewire Made in a Novel Micro-Pultrusion Process", Journal 2007, Germany.

Kraemer, N.A. et al., "Preclinical Evaluation of a Novel Fiber Compound MR Guide Wire", Journal, 2008, Germany.

Ladd, Mark E. et al., "Reduction of Resonant RF Heating in Intravascular Catheters Using Coaxial Chokes", Magnetic Resonance in Medicine Journal, 2000, pp. 615 to 619.

Hillenbrand, C.M. et al., "The Bazooka Coil: A Novel Dual-Purpose Device for Active Visualization and Reduction of Cable Currents in Electrically Conductive Endovascular Instruments", Journal, 2005.

Zanchi, M.G. et al., "An Optically-Coupled System for Quantitative Monitoring of MRI-Induced RF Currents into Long Conductors", Journal, 2008, U.S.A.

Turner, R., "A Target Field Approach to Optimal Coil Design", Letter to the Editor, May 2, 1986, pp. L147 to L151, Great Britain.

Dharmakumar et al., Visualization and Tracking of a Conventional Guidewire with Low Flip Angle SSFP Imaging: An Initial Study, Proc. Intl. Soc. Mag. Reson. Med. 17 (2009).

Griffin et al., Safely Assessing Radiofrequency Heating Potential of Conductive Devices Using Image-Based Current Measurements, 2014 Wiley Periodicals, Inc.

* cited by examiner

CATHETER FOR MAGNETIC RESONANCE GUIDED PROCEDURES

The present disclosure claims priority from U.S. Patent Application No. 61/095,974, filed Sep. 11, 2008, the entirety of which is hereby incorporated by reference

TECHNICAL FIELD

The present disclosure is related to a catheter for magnetic resonance guided procedures. In particular, the present disclosure is related to such catheters that provide magnetic resonance guidance using magnetic coupling.

BACKGROUND

With the emergence of real-time magnetic resonance imaging (MRI) techniques, the use of MRI has expanded from static diagnostic imaging to include the potential to guide a variety of interventions. Many percutaneous cardiovascular procedures (i.e., interventions performed with a catheter inserted into the vasculature) may benefit from guidance where MRI's soft tissue contrast may be exploited. One example is the traversing of chronic total occlusions in coronary and peripheral vessels. The presence of chronic total occlusions is the leading reason for selection of bypass surgery over less invasive interventions. Despite the benefits of percutaneous treatment, clinicians are often unable to traverse occlusions with catheter-based devices due to the inadequate imaging capabilities of X-ray fluoroscopy that is typically used to image such treatment.

Reference is now made to FIG. 1. Typically, during percutaneous interventions two pieces of equipment are inserted into the vasculature 10. The first is a catheter 12 that may be a long thin hollow tube. The second is a guidewire 14, which is typically thin flexible wire that may travel through the lumen of the catheter 12. FIG. 1 shows a schematic diagram illustrating the use of a conventional guidewire 14 and catheter 12 in the vasculature 10 of a patient. Typically, the guidewire 14 is extended from the catheter tip, and because the guidewire 14 is usually very flexible, it is the first device to be manoeuvred through the vasculature 10. The catheter 12 is advanced over top of the guidewire 14 to provide mechanical support, and when pushed, the catheter 12 follows the path of the guidewire 14.

Several MRI-guided guidewire tracking and visualization techniques have been proposed, which may be classified into two groups. The first group may be referred to as "passive techniques" where the device is made visible through the use of signal voids, susceptibility artifacts, or off-resonance signals (e.g., those discussed in References 1-4). These techniques typically are limiting in that the device must lie within the MR imaging plane in order to be viewed.

The second group may be referred to as "active techniques". Active techniques rely on an acquisition of the magnetic resonance (MR) signal from small micro-coils or wires located on the device in order to determine device position (e.g., as discussed in References 5 and 6). Active visualization techniques typically do not suffer from the same limitations as passive techniques due to the fact that the signal used for device localization is acquired independently from that used for anatomical imaging. This enables the device to be located even when it lies outside the current imaging plane. Moreover, because the signal from the device is a separate signal, it may be colour-overlaid on anatomical images to create a "positive contrast" that may be easy to identify and put in an anatomical context. However, active visualization of the guidewire may be challenging in that many of the techniques developed for catheters and endoscopes (e.g., the use of micro-coils) are difficult to translate to guidewires due to the limited thickness of guidewires. Guidewires are thin wires with a typical diameter of less than 0.035 inches, whereas catheters and endoscopes may have a much larger diameter which allow for accommodation of components necessary for this visualization.

Some current active guidewire designs consist of a loopless antenna that is formed on the end of a coaxial cable (e.g., Reference 7). This design includes two limitations. The first is that the active wires typically require significant internal structure. A result of this is that the mechanical properties of the guidewire do not resemble that of a conventional bare wire, which may affect its manoeuvrability in the vasculature. Further, active guidewires may be considered to be unsafe because resonant currents may develop on the outside conductor of the thin coaxial cable used to carry the MR signal from the loopless antenna to the input of the MR scanner (e.g., as discussed in References 8-11). These resonant currents may create intense localized heating of tissues located at the ends of the active guidewire. The same safety concern exists regarding the use of traditional non-active guidewires in the MR scanner.

Reference is now made to FIG. 2. A design for a MR-compatible guidewire 20 has been proposed that consists of a short non-resonant length of nitinol connected to a non-conducting fibreglass rod (e.g., as discussed in References 12 and 13). The non-conductive length may be made of any non-conductive material, including fibreglass, graphite, carbon fibre, or a polymer. FIG. 2 illustrates a schematic diagram of such a guidewire 20. In this schematic, the guidewire 20 has a non-resonant conductive length 22 (e.g., approximately 10 cm) of nitinol at the distal end attached to a non-conducting length 24 (e.g., a fibreglass rod) that forms the remaining length of the guidewire 20. The length of nitinol 22 is non-resonant and thus large currents are unable to develop in the guidewire 20. Such a guidewire 20 is therefore not susceptible to the heating concerns discussed above. Visualization of the guidewire 20 is done passively by doping the conductive length 22 and non-conductive length 24 with small iron particles. This creates a susceptibility artifact that may be seen on MR images. However, this method suffers from the same limitations as other passive visualization methods, including the limitation that the guidewire 20 may be visualized only when it is in the imaging plane.

SUMMARY

A catheter for magnetic resonance (MR) guided procedures is disclosed that addresses some of the challenges discussed above.

In some aspects, there is provided a catheter for magnetic resonance (MR) guided procedures comprising: a catheter body having a lumen for accommodating an intravascular device; a magnetic coupling component in the catheter body, the magnetic coupling component being designed to magnetically couple with a conductive length on the intravascular device, the magnetic coupling resulting in a signal; the catheter having a connection to deliver the signal to a processor.

In some aspects, there is provided a combination for magnetic resonance (MR) guided procedures comprising: the catheter described above; and a MR-compatible intravascular device designed to pass through the lumen of the catheter, the intravascular device having a conductive length; wherein the magnetic coupling component in the catheter is configured to magnetically couple with the conductive length, magnetic coupling between the magnetic coupling component and the conductive length resulting in a signal.

In some aspects, there is provided a method of monitoring a magnetic resonance (MR) guided procedure comprising: providing the combination described above located in a patient, the intravascular device having been inserted through the catheter; inducing a current in the conductive length; delivering a signal to a processor, the signal resulting from magnetic coupling between the magnetic coupling component and the conductive length.

There is also provided a use of the catheter and combination described above for performing a MR guided procedure.

DETAILED DESCRIPTION

A catheter for MR guided procedures is disclosed, including kits and methods using this catheter. As disclosed, a MR signal around a short conductive length on a device inserted through the catheter (e.g., a guidewire) is detected through the interaction of this conductive length and a magnetic coupling component, such as a coil (e.g., a toroidal-shaped coil), which may also be referred to as a "pick-up coil", to which the conductive length is magnetically coupled. Although the term "magnetic coupling" is used in this disclosure, it should be understood that magnetic coupling refers also to electric coupling, as the coupling is based on electromagnetic fields. The magnetic coupling component is located in the wall of a catheter through which the MR-compatible guidewire travels. The signal picked up by the magnetic coupling component is then delivered to a processor, such as a MR scanner or other external electronics, for processing. Signal processing may include filtering, digitization, reconstruction or analysis of the signal, as is common in the field of MRI. The magnetic coupling component may be connected to the receive chain of the MR scanner using a transmission line, such as a conventional coaxial cable located inside the guide catheter.

Figure 1:
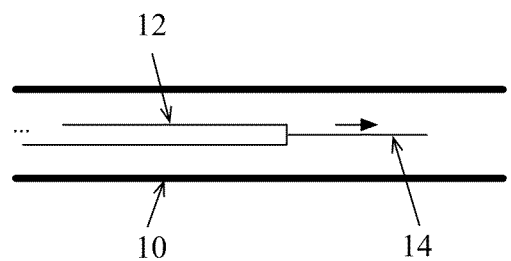
FIG. 1 shows an example prior art catheter and guidewire arrangement.
Figure 2:
FIG. 2 shows an example prior art MR compatible guidewire.
Figure 3:
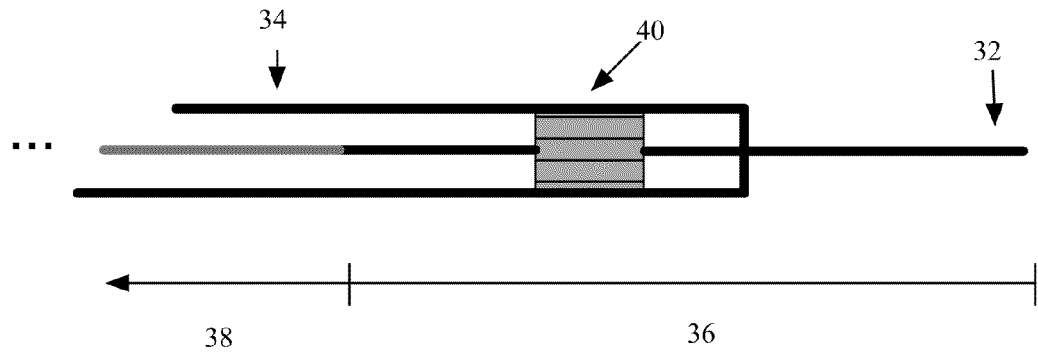
FIG. 3 shows a schematic diagram of an example MR guided guidewire and catheter.

Reference is now made to FIG. 3 showing a schematic diagram of an example MR guided guidewire 32 and catheter 34. The guidewire 32 has a conductive non-resonant length 36 (e.g., a length of nitinol), and a non-conductive length 38. To perform active visualization of MR guided guidewires, a magnetic coupling component 40, in this example a small rectangular toroidal coil, embedded in the wall of the catheter 34, is used to detect currents induced on the conductive length 36 of the guidewire 32. Although a guidewire 32 is shown in this example, the conductive length 36 may be provided on other devices that may pass through the catheter 34, including balloons, needles and other similar intravascular devices. This disclosure will refer to a guidewire 32 as an example of the device passing through the catheter 34, but it will be understood that all references to a guidewire 32 also applies to other devices that may pass through the catheter 34.

In general, the guidewire may be any suitable MR-compatible guidewire having a conductive length (e.g., at the distal end) and its remaining length being non-conductive. The conductive length should be a non-resonant length (e.g., in order to be MR-compatible), which may be dependent on several variables, including the diameter of the guidewire and the electrical properties of the guide catheter, as well as the MR system it is to be used in. For example, a non-resonant length for the conductive length may be in the range of about 1 to 30 cm. Typically, such a guidewire is designed to be MR-compatible by limiting the conductive length to be less than a resonant length. Nitinol has been used as the material for the conductive length, in order to best approximate the behaviour of conventional nitinol guidewires, however other conductive materials may be used for the conductive length, including copper, stainless steel, gold, platinum, and combinations thereof.

In general, the catheter is suitably sized to allow the guidewire to pass through its lumen. The diameter of the catheter may be designed to facilitate intravascular procedures in certain parts of the vasculature. For example, the catheter may have a smaller diameter where it is designed to be used in the coronary vessels, and may have a larger diameter where it is designed to be used in the peripheral vessels. Typically, the average lumen diameter of the coronary arteries in an adult is about 1.5 to 2.5 mm, and the peripheral lumen diameters (e.g., that of the common femoral artery) may be as large as 5 mm. Thus, the catheter may be sized to suit these vessels or larger anatomical structures (e.g., the trachea or the colon), for example the catheter may have an outer diameter in the range of about 1.5 mm to about 5 cm, in some examples in the range of about 3 mm to about 5 mm, depending on intended use.

The catheter has a magnetic coupling component (e.g., located at its distal end). The magnetic coupling component is designed to be magnetically coupled to the conductive length of the guidewire, as will be explained below. The magnetic coupling component in some examples is positioned on the catheter to correspond to the likely position of the conductive length on the guidewire. The magnetic coupling component may be made of any suitable conductive material, such as copper, nitinol, aluminum, or any other suitable material. Copper may be useful since the magnetic susceptibility of copper is such that it does not produce image artifacts in MR images. The magnetic coupling component may also include other materials to provide mechanical support. Additional materials may be bio-compatible polymers, including polyetheretherketone, delrin, polyimide, polyvinylchloride, polyethylene, polycarbonate, polysulfone, polypropylene, polytetrafluoroethylene, combinations thereof, or any other suitable polymer. The magnetic coupling component may also be made using flexible laminates, for example a flexible copper clad laminate. Using a flexible material may result in a flexible magnetic coupling component, which may help the catheter to maintain flexibility.

The magnetic coupling component may be a coil, such as a toroidal coil, though it is understood that other component and/or coil shapes can be used to achieve the magnetic coupling as explained below. In general, the magnetic coupling component is designed so that it magnetically couples to the conductive length on the guidewire that travels through the catheter. This can be achieved by designing a magnetic coupling component that produces a magnetic field that overlaps with the magnetic field produced when a current flows through the conductive length, as will be described further below. Mathematically, this corresponds to designing a magnetic coupling component such that the dot product (i.e., scalar product) of the magnetic field produced when unit flows through the conductive length is non-zero when integrated over all points in space. In this situation, it may be said that there is mutual inductance between the magnetic coupling component and the conductive length.

Figure 4:
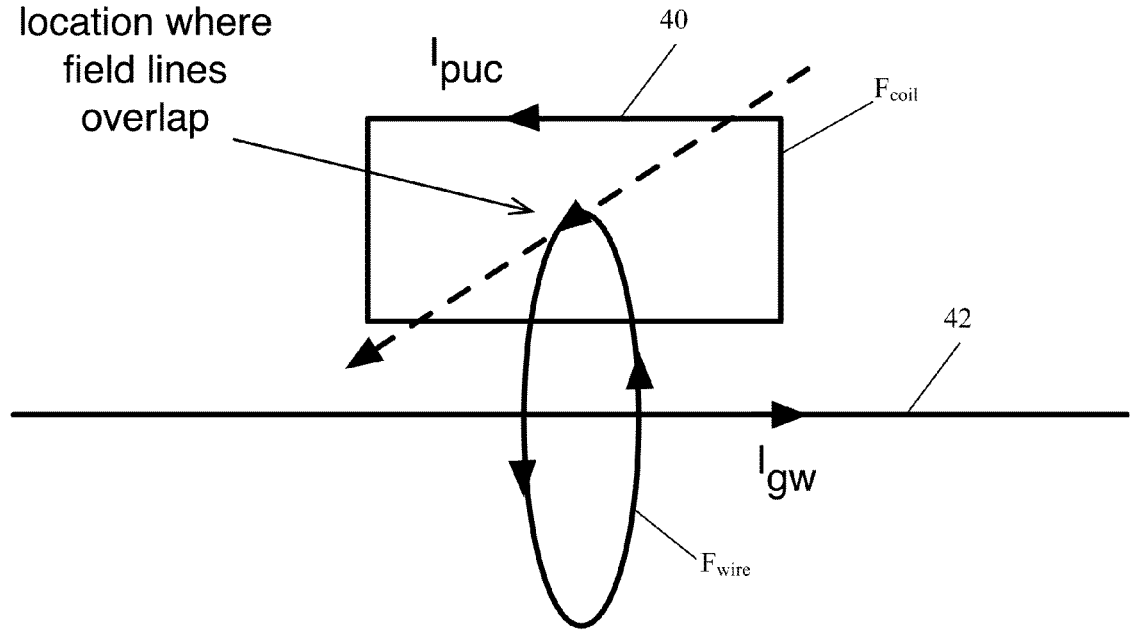
FIG. 4 is a schematic illustration of magnetic coupling of an example magnetic coupling component.

This concept is illustrated for the example of the magnetic coupling component 40 being a single loop coil located adjacent to a conductive wire 42 in FIG. 4. In the example shown, the conductive wire 42 has current $I_{wire}$ flowing through, giving rise to an electromagnetic field. One example set of field lines $F_{wire}$ is shown for the conductive wire 42. The magnetic coupling component 40 has current $I_{coil}$ flowing through, giving rise to an electromagnetic field. One example set of field lines $F_{coil}$ is shown for the magnetic coupling component. The overlap between $F_{wire}$ and $F_{coil}$ gives rise to non-zero inductance between the magnetic coupling component 40 and the conductive wire 42.

Based on this general theory, the magnetic coupling component may be designed using typical calculations and/or simulations. For example, the Target Field Method, which solves for a current distribution that would produce a specified magnetic field, may be used (for example, as described in Turner, *J Phys. D: Appl. Phys.* 19:147-151, 1986.).

The magnetic coupling component may be sized to suit the diameter of the catheter as discussed above. Although the disclosure has referred to a catheter as having the magnetic coupling component, other interventional devices through which an intravascular device can pass, such as sheaths, may be used to carry the magnetic coupling component, and the magnetic coupling component may be sized accordingly to fit these other devices. For example, the magnetic coupling component may be in the range of about 0.3 mm to about 5 cm in diameter, such as in the range of about 1 mm to about 10 mm in diameter. The magnetic coupling component may be designed to have a length that does not interfere or otherwise affect the behaviour, such as the flexibility, of the catheter. For example, for a rigid magnetic coupling component (e.g., a rigid coil), the magnetic coupling component may be limited to a length of about 0.1 mm to about 10 mm, but may have a greater length where flexibility of the catheter is not important (e.g., for use in substantially straight vessels). Where the magnetic coupling component is flexible, there may be no such limit on the length of the magnetic coupling component. A greater length for the magnetic coupling component may allow for greater magnetic coupling between the magnetic coupling component and the conductive length, which may result in a stronger signal and better imaging.

Although the catheter has been described as having a magnetic coupling component at or near its distal end, the magnetic coupling component may be provided anywhere along the length of the catheter. It may be useful to position the magnetic coupling component close to where the conductive length of the guidewire is expected to be, as the magnetic coupling between the conductive length and the magnetic coupling component typically is stronger when the magnetic coupling component is located at or near to the center of the conductive length. The coupling between the magnetic coupling component and the conductive length typically decreases in strength with radial distance between the conductive length and the magnetic coupling component. For example, a radial distance in the range of about 0.1 mm to about 1 cm may provide for a suitably strong magnetic coupling.

Figure 17:
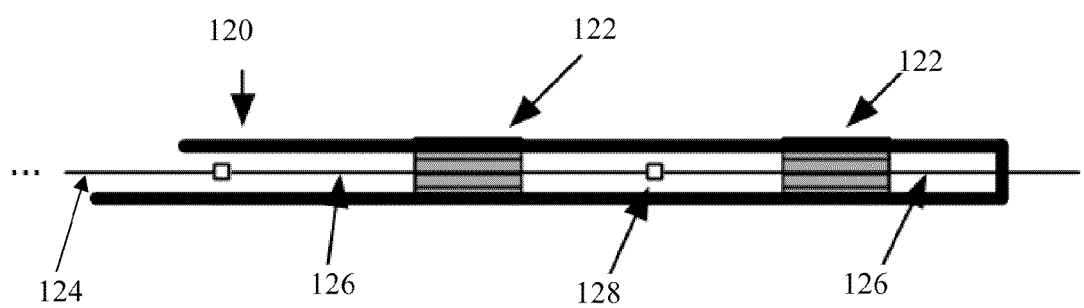
FIG. 17 is a schematic illustration of an example MR guided guidewire and an example catheter having more than one conductive length and magnetic coupling component.

The catheter may have more than one magnetic coupling component. For example, the catheter may have one magnetic coupling component at or near its distal end, and additional one or more magnetic coupling components down its length, such as the example illustrated in FIG. 17. As shown, the catheter 120 may have two or more magnetic coupling components 122 along its length. The magnetic coupling components 122 in this example are shown together with a device 124 (e.g., a guidewire) passing through the catheter 120 that has multiple conductive lengths 126. The conductive lengths 126 on the device 124 are segments separated by isolating joints 128. The conductive lengths 126 may also be separated by non-conductive lengths (not shown). The use of additional magnetic coupling components 122 may allow the detection of a single conductive length 126 at different points along the catheter 120, for example as the device 124 passes through the catheter 120, or to detect the position of several conductive lengths 126 on a single device 124.

In general, a method for visualization of a MR guided guidewire is disclosed. A MR compatible device, such as a guidewire, having a non-resonant conductive length at or near its distal end is passed through a catheter having a magnetic coupling component (e.g., located at or near its distal end) such that the conductive length is magnetically coupled to the magnetic coupling component. During the acquisition of MR signal (e.g., as part of conventional MRI), a current is induced in the conductive length. Due to magnetic coupling between the conductive length and the magnetic coupling component, this current induces a voltage signal across the leads of the magnetic coupling component. The signal from the magnetic coupling component is transmitted to the receive chain of the MR scanner, for example using conventional transmission lines or a coaxial cable in the catheter. This signal may then be processed using conventional signal processing techniques to obtain an image of the conductive length. This signal may also be processed in other ways as will be discussed further below.

Instead of using a transmission line to deliver the signal from the magnetic coupling component, other signal delivery techniques may be used. For example, the signal may be delivered using an optical fibre or other common signal delivery means.

Using the disclosed catheter, the guidewire does not require any internal structure (e.g., any electronic components or cables) as it is not itself being used as a transmission line. This avoids the need to add components to a small-diameter wire, and avoids affecting the handling behaviour of the guidewire. Safety concerns regarding the use of conducting structures are not associated with the guidewire since the conductive length is kept to a non-resonant length. The catheter may be used with any guidewire or other intravascular device that is MR-compatible and has a conductive length (e.g., at or near its distal end) that may pass through the catheter. The magnetic coupling component in the catheter may be designed to magnetically couple and hence detect any such conductive length, as will be described below.

Since the magnetic coupling component is provided in the catheter, size constraints which limit possible safety features when a transmission cable is connected directly to the guidewire are diminished since the cable is now inside the larger catheter. Thus, additional components may be added to the catheter to further improve the safety and/or signal quality without burdening the guidewire. For example, RF chokes (e.g., as discussed in Reference 14), baluns or other devices that reduce currents on the outer conductor of the cables may be incorporated into the catheter to further reduce any safety concerns. Thus, the disclosed catheter provides the benefits of active visualization for MR guided procedures yet retains the safety associated with passive MR-compatible guidewires.

Theory and Design

Figure 5:
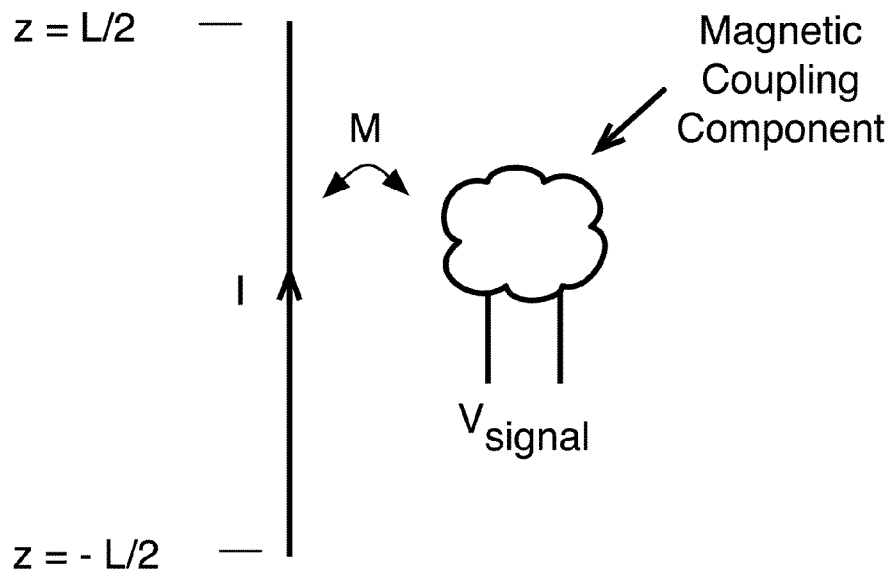
FIG. 5 is a schematic illustration of magnetic coupling of another example magnetic coupling component.

A theory of operation is now presented. The present disclosure is not bound or in any way limited by the theory presented. This theory may be useful in designing the MR guided guidewire and/or catheter. With reference to FIG. 5, consider a short conducting segment of wire of length L positioned adjacent to a magnetic coupling component, in this example a coil, that is magnetically coupled to the wire such that a mutual inductance M exists between the wire and the coil.

The sensitivity to magnetization surrounding the conductive length of the guidewire can be analyzed through the use of reciprocity and the calculation of the current induced along the conducting segment given a input current I at the magnetic coupling component or its peripheral circuitry.

Figure 6:
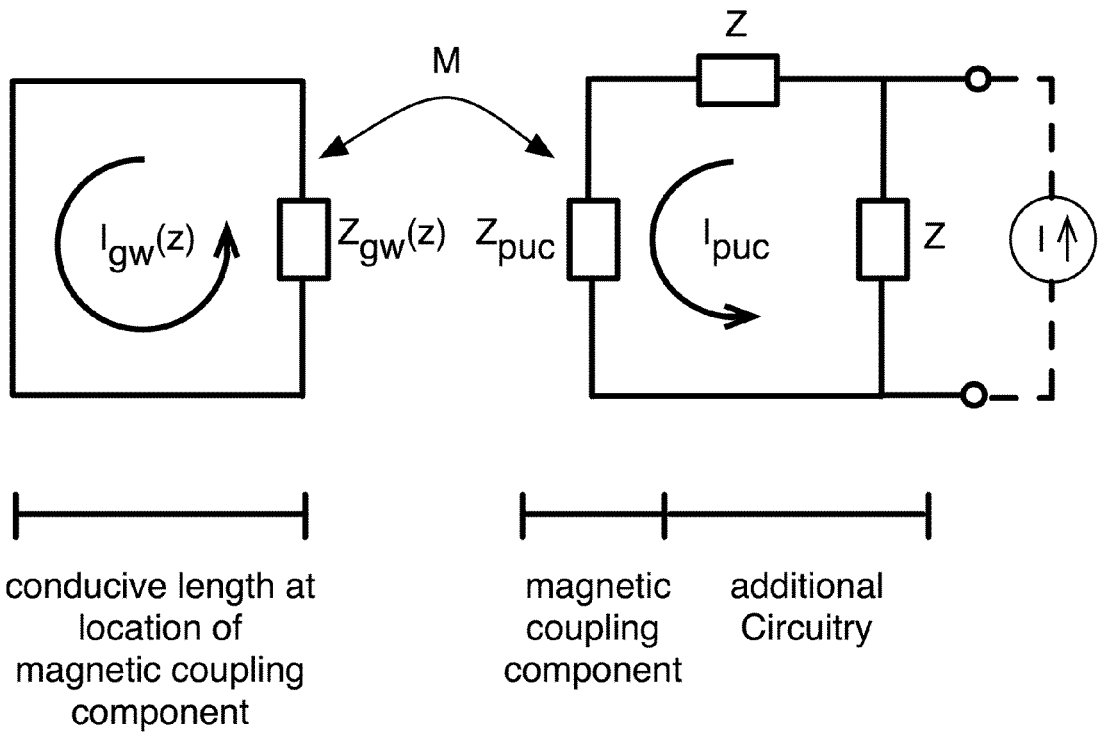
FIG. 6 is a schematic illustration modeling magnetic coupling of another example magnetic coupling component.

A simplified lumped-element model of the system is depicted in FIG. 6. In this example, the magnetic coupling component is a coil. Here, $Z_{gw}(z)$ is the complex impedance of the wire at the location z of the coil, $I_{gw}(z)$ is the current in the conductive length at the location z of the coil, M is the mutual inductance between the conductive length and the coil, and $Z_{puc}$ is the complex impedance of the coil. Other local tuning elements present are in this model. The impedance of the conductive length at a particular z location $Z_{gw}(z)$ is dependant on several factors including (but not limited to) the length of the conductive length and the surrounding environment and can be numerically calculated using numerical methods such as the Method of Moments (MoM). The current in the coil ($I_{puc}$) can be solved using conventional circuit analysis techniques and once known, the current distribution along the entire length of the conductive length can be determined using numerical methods.

The spatial sensitivity to MR signal in the vicinity of the conductive length can be calculated given the current distribution along the conductive length by calculating the component of the magnetic field perpendicular to the static field of the MRI produced by the current in the guidewire, for example using the law of Biot-Savart or any other suitable conventional methods.

The equations governing the mutual inductance and the current in the magnetic coupling component may be used to design the magnetic coupling component. For example, the dimensions of the magnetic coupling component may be adjusted where a certain distance between the magnetic coupling component and the conductive length is desired. Using the above theoretical description and lumped-element circuit element model, a variety of magnetic coupling components (e.g., different coil configurations) and circuit configurations may be designed for different applications, having different geometries and dimensions, in order to achieve the presently disclosed MR guided guidewire and catheter. It should be noted that the current on the guidewire is dependent on circuitry connected to the magnetic coupling component and a person skilled in the art would know how to apply the model for different configurations and adapt the model and the corresponding equations accordingly.

Design Example

Figure 7A:
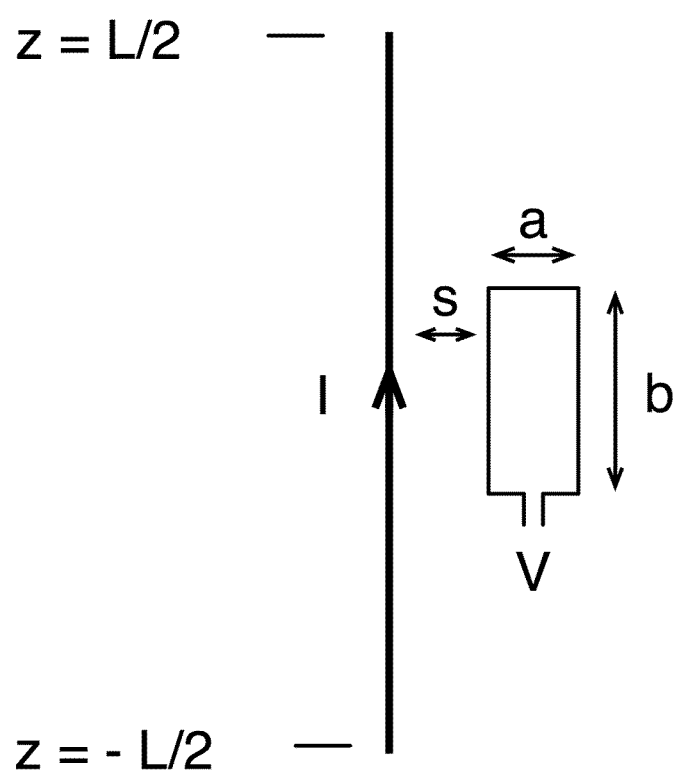
FIG. 7A shows a schematic modeling an example magnetic coupling component and a conductive wire.

One example of a magnetic coupling component designed to magnetically couple to a conducting length is a rectangular-shaped toroidal coil with N turns each of length b, width a, and distance s from the conductive length. With this particular magnetic coupling component design, an intravascular device passing through the centre of the toroidal coil will magnetically couple with the magnetic coupling component. An illustration of this example magnetic coupling component, in the form of a coil, is shown in FIG. 7A. For simplicity, only one turn is shown. The mutual inductance M between the coil with N turns can be shown to be:

$$M = \frac{\mu N b}{2\pi} \ln\left(\frac{s+a}{s}\right) \qquad \text{[eqn 1]}$$

Along with the impedance of the magnetic coupling component and the properties of the conducting segment, one can use the theory above to predict how the configuration will behave. Although this is only one example, any other suitable magnetic coupling component (e.g., having a coil design) can be designed to further increase the mutual coupling M to improve the signal acquired from the magnetic coupling component.

Other examples of a magnetic coupling component, for example based on the theory described above, may include (but are not limited to) single or multiple loops of wire and single or multiple loops of conductive ribbon.

Figure 7B:
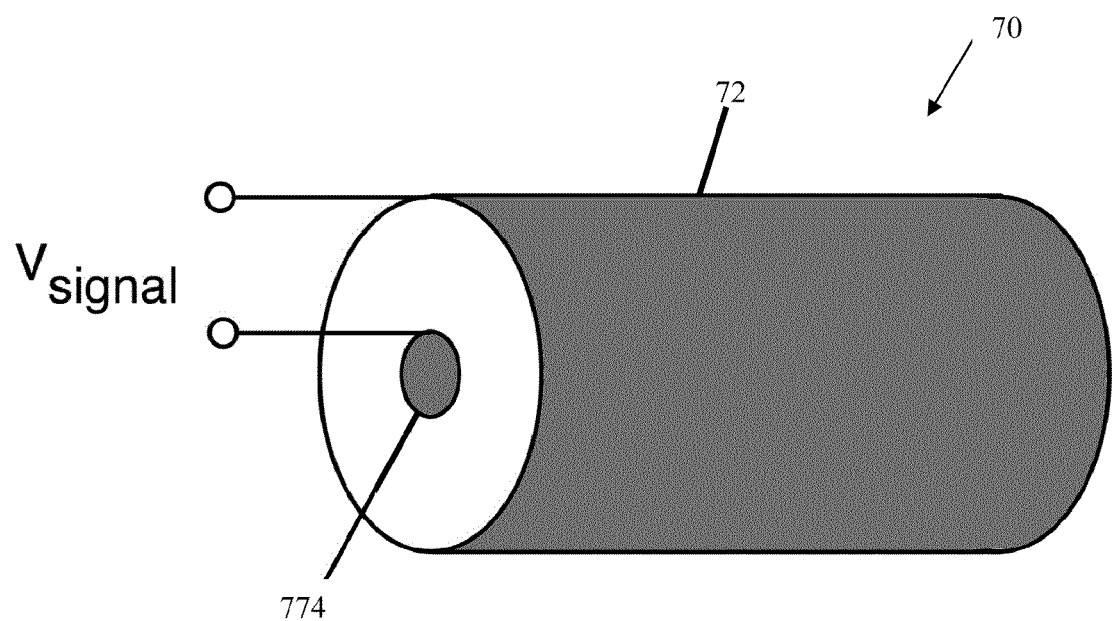
FIG. 7B shows a schematic of an example magnetic coupling component.

FIG. 7B illustrates an example of a suitable magnetic coupling component 70. In this example, the magnetic coupling component 70 is generally in the shape of a cylinder with a hole through its length. In this example, the magnetic coupling component 70 includes two concentric conductive tubes 72, 74, that are joined to each other at one end of the cylinder (not shown). The conductive tubes 72, 74 are spaced apart by a non-conductive material. The material separating the two tubes, in some examples could be air or alternatively could be some type of plastic or any other type of suitably non-conductive supporting material. In operation, a signal (in this example, denoted $V_{signal}$) is measured as a voltage across the two conductive tubes 72, 74 at the end where the conductive tubes 72, 74 are not joined. In some examples, the magnetic coupling component 70 may have dimensions that are similar to the coil design described further below. For example, the outside diameter of the magnetic coupling component 70 may be designed such that it fits inside a catheter and may be in the range of about 0.3 mm to about 5 cm. The length of the magnetic coupling component 70 may be in the range of about 0.1 mm to about 10 cm. To improve efficiency of magnetic coupling, the diameter of the inner conductive tube 74 may be configured to be as small as possible while still allowing the intended interventional device to pass through it. Additional circuitry, for example capacitors, may be added to the magnetic coupling component 70 to form a resonant circuit, according to conventional methods.

Compared to a coil design, for example the design described below, this example magnetic coupling component 70 may exhibit a lower degree of magnetic coupling with the interventional device, resulting in lower efficiency. However the magnetic coupling component 70 may provide a lower resistance, resulting in greater efficiency. Any efficiency gains or loses associated with these properties of the magnetic coupling component 70 may be modeled, for example using the theory described above. The design of the magnetic coupling component 70 may be relatively easier to manufacture on a smaller scale, for example by simply plating a machined piece of plastic, compared to a coil design.

EXAMPLES

Figure 8:
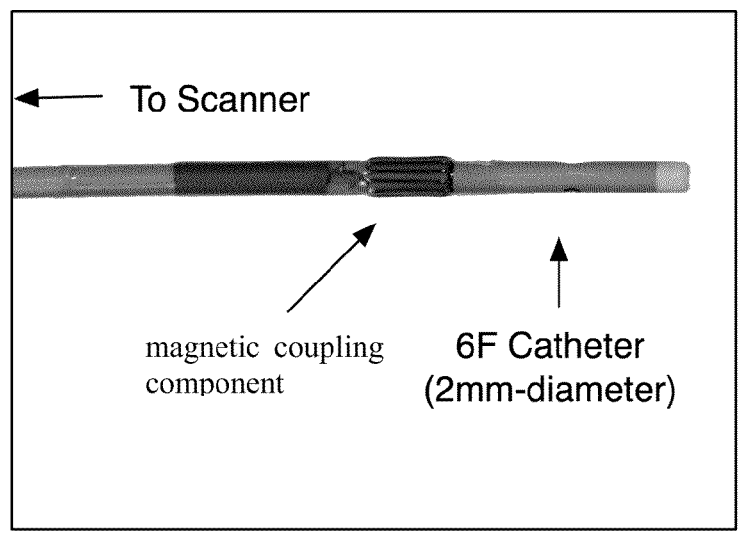
FIG. 8 is an image of an example catheter.

An example of the MR guided guidewire and a catheter having a suitable magnetic coupling component is shown in FIG. 8. In this example, the magnetic coupling component is a toroidal pick-up coil, having a width of 1 mm, length of 5 mm and 12 turns, built using 36 AWG insulated magnet wire (e.g., copper wire) and embedded in the wall of a typical 6F diagnostic catheter (e.g., MP1 from Cordis). The magnetic coupling component was connected to electronic circuitry, in this case a matching network that was located at the proximal end of the catheter, and then to the MR scanner via a length of 0.3 mm-diameter coaxial cable. This catheter was used with a MR-compatible guidewire having a nitinol conductive length of length 15 cm, which may be passed through the lumen of the catheter.

Figure 9:
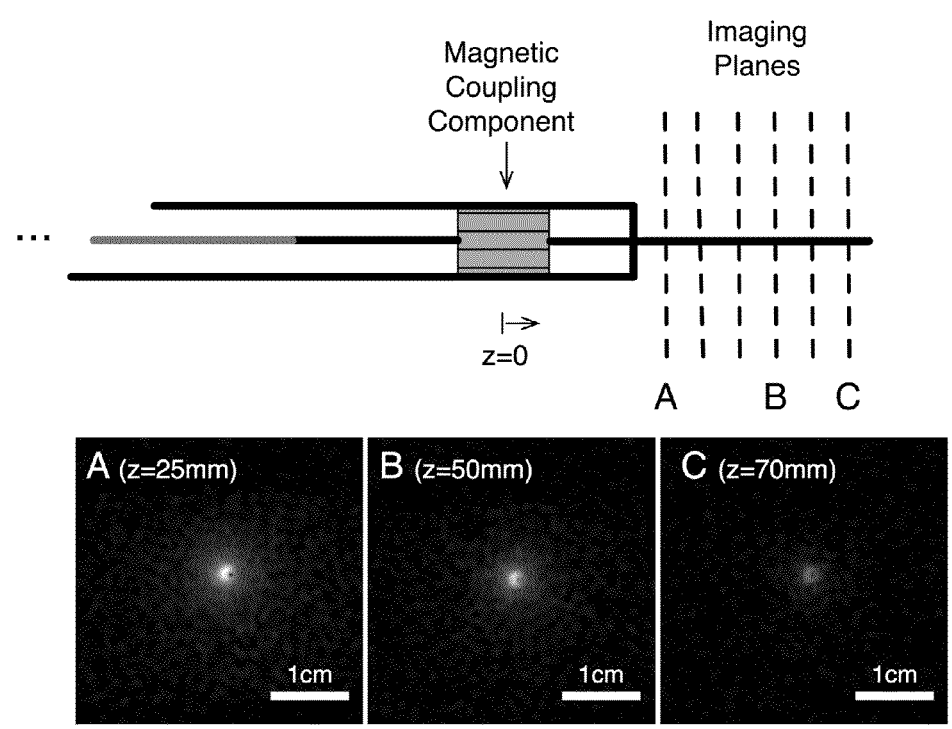
FIG. 9 is a schematic of an example MR guided guidewire and catheter, and images demonstrating the visualization of the guidewire.

The catheter and guidewire were placed in a 0.4% saline bath and images were acquired in cross-sectional planes through a portion of the wire that extended from the catheter tip. These images are shown in FIG. 9. An SPGR MRI pulse sequence was used to acquire these images, with TR=50 ms, TE=6 ms, FA=30, FOV=12 cm, Resolution=469 µm. Significant MR signal in the region immediately surrounding the wire may be seen thereby making the guidewire visible.

Figure 10:
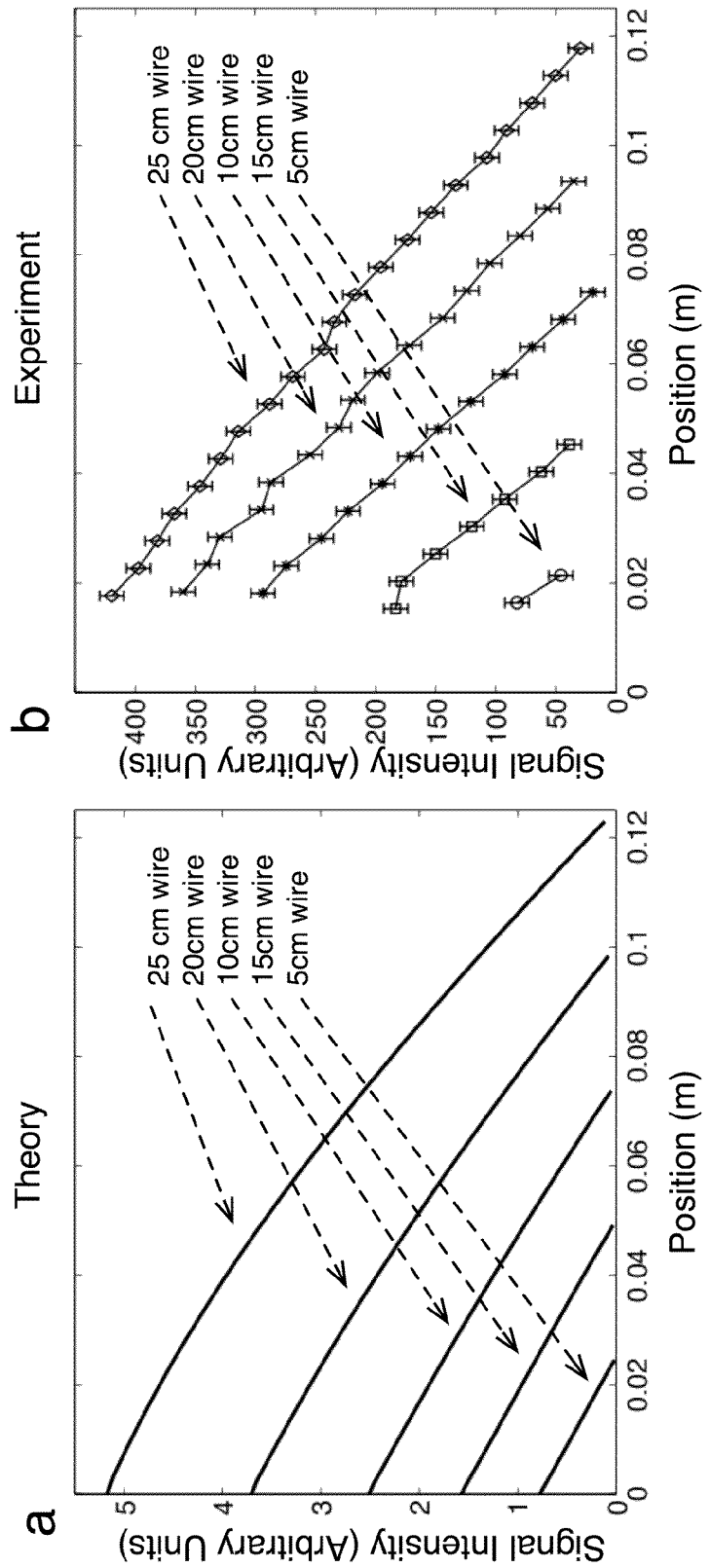
FIG. 10 are charts illustrating signal intensity in example MR guided guidewires, compared to theory.

Reference is now made to FIG. 10. In addition to the above demonstration, further experiments were done to compare the behaviour of the technique to the theory described above. Five lengths (5, 10, 15, 20, and 25 cm) of 0.018"-diameter nitinol wire were extracted from a conventional guidewire (e.g., Glidewire, Terumo) and were centred in the magnetic coupling component, in this example a coil. The coil and wire were submersed in 0.4% saline. Images were acquired in cross-sectional planes through the axis of the guidewire in front of the coil with the wires aligned along the direction of the static field. The average signal intensity inside a circular region of interest (0.15 $cm^2$) centred about the wire was measured in each of the images and results were compared to theory. Signal around the wire was found to increase as the length of the wire approached a resonant length, as indicated in FIG. 10*b*. It should be noted that the signal in the region around the wire decreases as the imaging plane approaches the tip of the wire. This is due to the current distribution in the wire which approaches zero at the wire ends and is maximum at the centre of the wire. The results were found to generally match those predicted by theory, as indicated in FIG. 10*a*.

Figure 11:
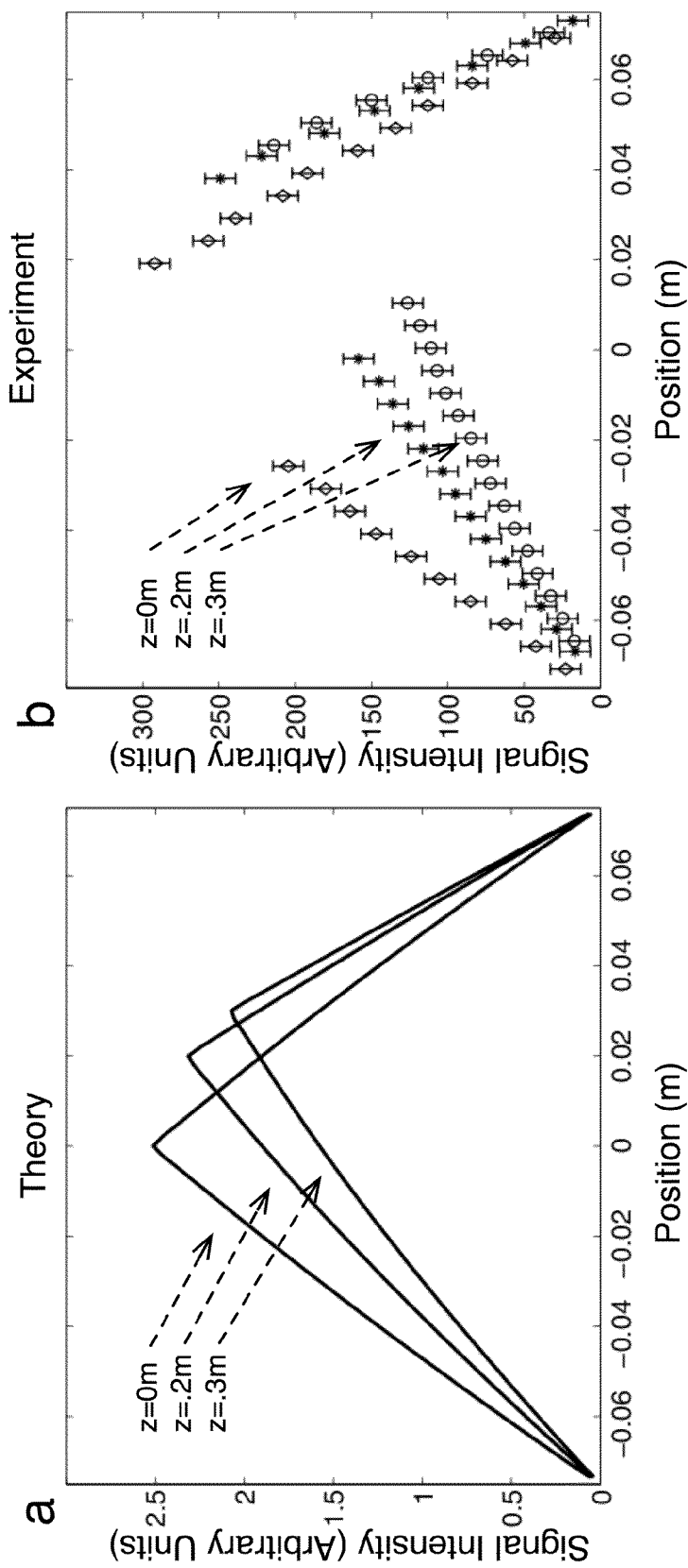
FIG. 11 are charts illustrating signal intensity in an example MR guided guidewires, compared to theory.

Reference is now made to FIG. 11. The 15 cm wire was placed in the coil and the coil was moved off-center by various amounts (0 cm, 20 cm, 30 cm). Images were acquired along the length of the wire to investigate the associated signal behaviour when the coil is positioned at different positions along the wire. The effects of positioning the coil at off-centre locations along the wire were also found to match those predicted by theory, as indicated in FIGS. 11*a* and 11*b*.

Viewing in Anatomical Context

Figure 12:
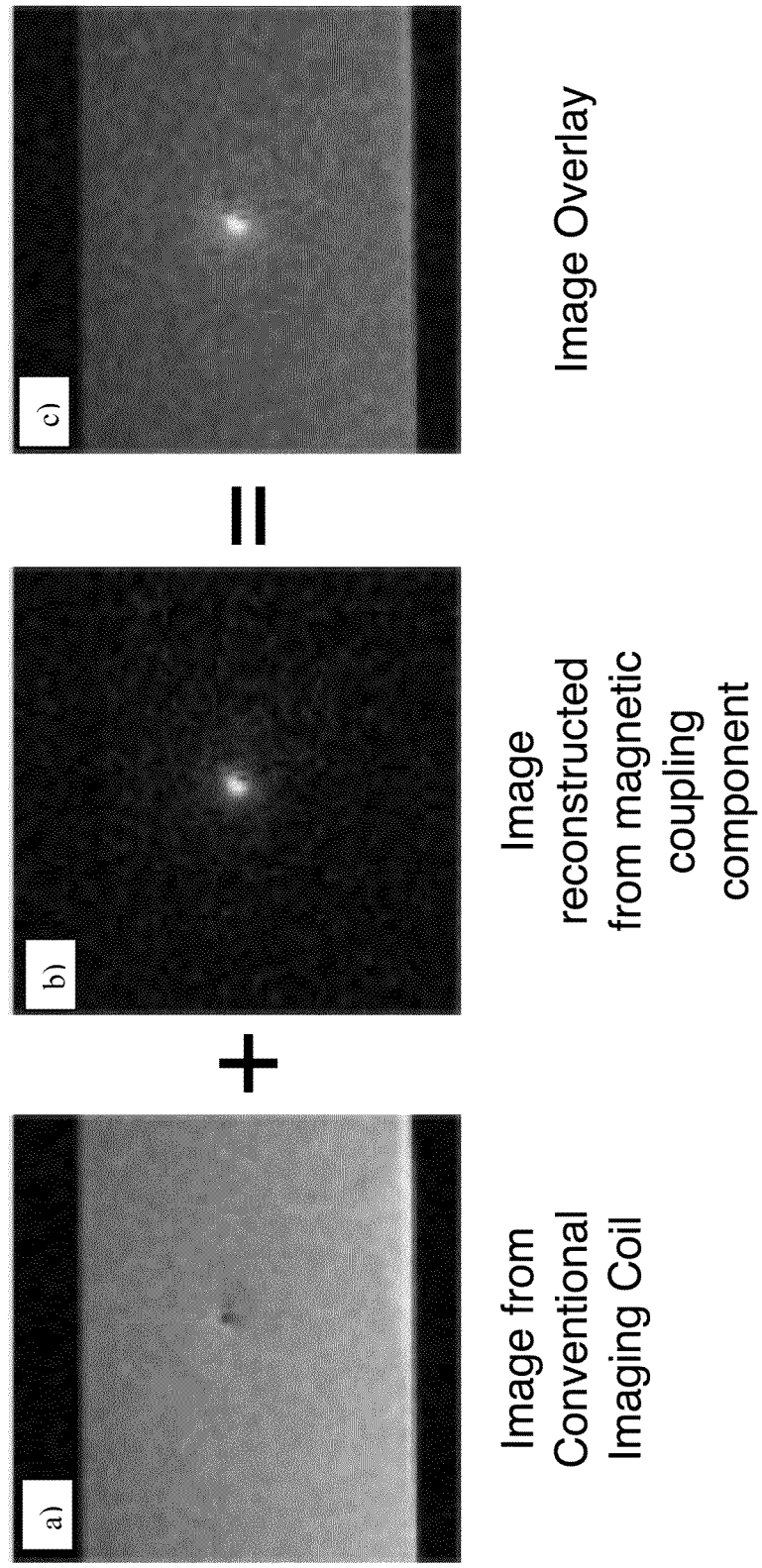
FIG. 12 shows images demonstrating the visualization of an example MR guided guidewire using a colour-overlay technique.

Reference is now made to FIG. 12, which illustrates an example of how the disclosed device may be used to visualize a guidewire in an anatomical context using a colour-overlay technique. In order to visualize the guidewire in an anatomical context (e.g., as may be required for guidance purposes) one may colour-overlay the images acquired from the magnetic coupling component onto anatomical images acquired using conventional surface coils in a MR system. In a phantom example, FIG. 12*a*) shows a conventional image obtained from convention MR surface imaging coils. FIG. 12*b*) shows an example image of the guidewire obtain using the disclosed device, with a red colour. FIG. 12*c*) shows the images imposed on each other. The signal from the magnetic coupling component may be transmitted to the MR scanner as a channel separate from the surface coils. This may allow the magnetic coupling component signal to be processed directly together with the signal from the surface coils using conventional image processing software, obtaining an anatomical image including indication of the guidewire. Alternatively, the magnetic coupling component signal may be processed separately from the surface coil signals, so that additional or different processing techniques may be applied to the magnetic coupling component signal, and the resultant image information from the magnetic coupling component may then be superimposed on the anatomical image from the surface coil, using conventional post-processing techniques.

Figure 13:
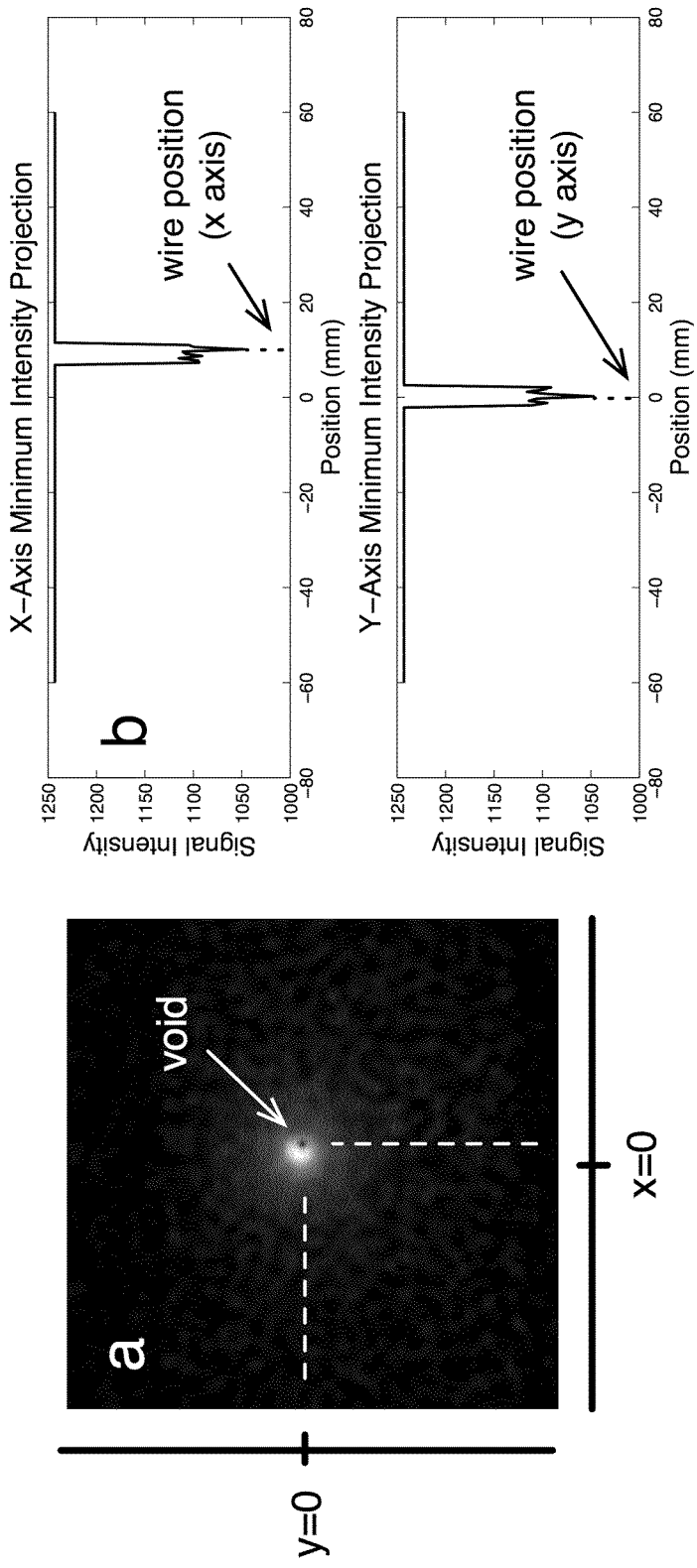
FIG. 13 shows images and signal plots demonstrating the visualization of an example MR guided guidewire using a minimum projection technique.
Figure 16:
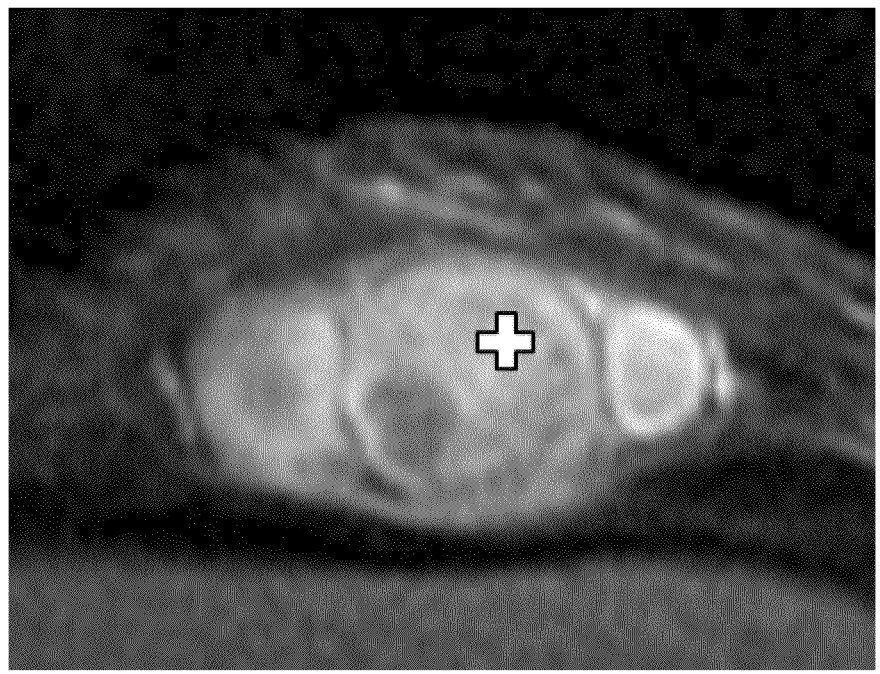
FIG. 16 is a simulation of an image that may be acquired using an example MR guided guidewire and an example catheter having intravascular imaging capabilities.

Reference is now made to FIG. 13. The position of the guidewire may also be found through the identification of a small signal void created by the presence of the guidewire. With active tracking techniques such as this, a region of high signal intensity surrounds the small signal void. This technique calculates the position information of the guidewire based on the image obtained from the magnetic coupling component. One method of finding the position of the void with high accuracy is to mask the image based on an intensity threshold and perform a minimum-intensity projection of the masked image. In the example shown in FIG. 13*a*), the original image showing the location of the guidewire is threshold masked, so that the high-intensity signal indicating the location of the guidewire is isolated. In FIG. 13*b*), the mask is inverted to obtain a void corresponding to the location of the guidewire (the corresponding signal is shown in FIG. 13*d*). In FIG. 13*c*), the void is identified using minimum intensity projections. The location of the minima corresponds to the void position. This process, or any other similar process, may be done automatically and/or in real-time, for example using convention image processing software. This technique calculates the location of the void position reflecting the position of the guidewire. Once this information has been calculated, the position of the guidewire may be displayed on anatomical images, such as by superimposing on the image obtained from surface coils, with any mark or symbol, including one or more 2-dimensional or 3-dimensional shapes (e.g., as shown in FIG. 16, described further below).

Additional Components

Additional components may also be incorporated into the disclosed catheter. For example, electronic circuits such as flexible circuit boards and elements such as capacitors may be included in the catheter to tune the magnetic coupling component, in order to increase the strength of the signal. Possible components include electronic components such as an amplifier circuit, a tuning circuit, a detuning circuit, a matching network, a filter circuit, an encoding circuit, and a current suppression circuit. A safety component may also be added, for example a RF choke or a balun. Components may also include preamplifiers to dynamically amplify the signal from the magnetic coupling component before it is transmitted through the coaxial cable. Components may also include diodes to detune the magnetic coupling component during the RF transmission phase of the MR imaging sequence, to avoid overheating of the magnetic coupling component. Components included in the catheter may also be designed to apply an alternating voltage to the magnetic coupling component to induce currents on the conductive length of the guidewire. For example, this may be used to oppose and thereby suppress currents induced on the conductive length of the guidewire during the transmit phase of the MR imaging sequence. Components may also provide for filtering of the signal or encoding of the signal before it is received at the processor.

Figure 14A:
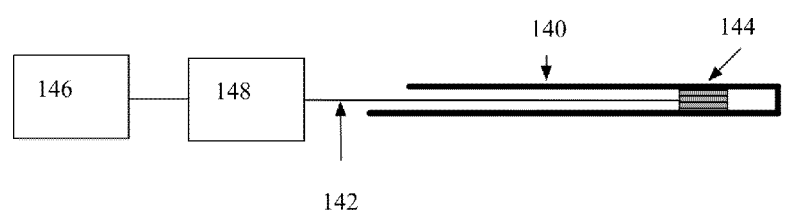
FIGS. 14A and 14B are schematic diagrams of example catheters having additional circuitry.
Figure 14B:
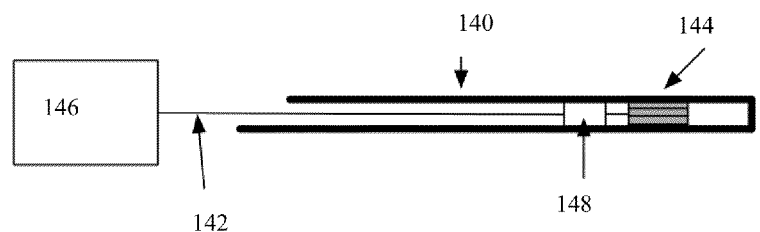

Reference is now made to FIGS. 14A and 14B. These are schematic diagrams showing how example additional components, in this case electronic circuitry, may be added to the disclosed catheter 140. As shown, there is a transmission line 142 between the magnetic coupling component 144 (in this example, a coil) and the MR scanner 146 for transmission of the signal detected at the magnetic coupling component. In FIG. 14A, the catheter 140 is provided with additional circuitry 148 (for example, a matching network and/or preamplifiers) near the proximal end of the catheter 140, via the transmission line 142 (e.g., a coaxial cable). The signal from the magnetic coupling component 144 reaches the additional circuitry 148 (e.g., for signal preprocessing) before being directed into the MR scanner 146 for image acquisition. In FIG. 14B, the additional circuitry 148 is still provided via the transmission line 142, but is embedded within the catheter 140, for example proximal to the magnetic coupling component 144. Embedding the circuitry 148 within the catheter 140 may make for a more compact device, but may limit the size and/or number of additional circuitry 148 added. Embedding the circuitry 148 within the catheter 140 also may allow pre-processing of the signal from the magnetic coupling component 144 to take place before the signal travels down the length of the transmission line 142. This may improve the signal-to-noise ratio of the signal and the visualization provided.

The catheter may be fabricated to include other devices or components. As described above, additional components such as RF-chokes may be included to increase the safety of the catheter. Another example is the inclusion of radio-opaque markers, for example at the distal end of the guidewire and/or catheter, to make the guidewire and/or catheter more visible under X-ray fluoroscopy.

Figure 15:
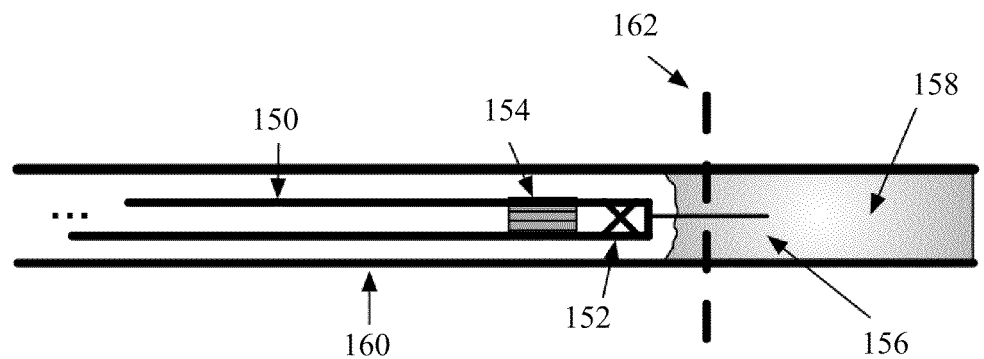
FIG. 15 is a schematic diagram of an example MR guided guidewire and an example catheter having intravascular imaging capabilities.

In some examples, the catheter includes one or more additional imaging coils. Reference is now made to FIG. 15, which shows a schematic diagram of an example catheter 150 for MR guided procedures having intravascular imaging capabilities. In this example, the catheter 150 is additionally provided with one or more intravascular imaging coils 152, in this example distal to the magnetic coupling component 154. In the example shown, a MR-compatible guidewire 156 passes through the catheter 150 into an occlusion 158 in a vasculature 160 of a patient. The imaging coils 152 may allow the acquisition of high-resolution images at an imaging plane 162 close in front of the catheter 150, and may provide details that are not clear or obscure using surface coils of the MR system alone. Although not shown, there may be additional transmission lines to deliver the intravascular imaging signal to the MR scanner. Such a device may be useful for revascularization of a chronic total occlusion 158. As the guidewire 156 is advanced from the catheter 150, the position of the guidewire 156 may be indicated on the intravascular image. This technique may help to guide manipulation of the guidewire 156, for example to ensure that the guidewire 156 is intraluminal before advancing another device over the guidewire 156.

FIG. 16 is a simulation of an image that may be acquired using a MR-compatible guidewire and the disclosed catheter with intraluminal imaging capabilities, for example as described above. Here, the position of the guidewire, as determined using the magnetic coupling component, is shown using a "+" marker. The position of the marker may be calculated using the small signal void as described above, or by using any other suitable techniques, and the marker may then be superimposed on the intravascular image acquired using the intravascular imaging coils in the catheter. Thus, a clear image is provided to help guide manipulation of the guidewire.

Imaging Using Magnetic Coupling Component

In addition to using the magnetic coupling component to detect the position of the conductive length, this arrangement may also be used to obtain anatomical images in the region surrounding a MR-compatible guidewire passing through the catheter. The signal immediately surrounding the conductive length has a large signal intensity. As such, instead of or in addition to using this signal to detect the position of the conductive length, this signal may be used to acquire images in the region around the conductive length. The signal may be used to produce a spatial map of MR signal, and this map may be used to produce images of the region around the conductive length. For example, the vessel wall, plaque, or occlusive materials in regions located adjacent to and beyond the tip of the guide catheter may be viewed. In some examples, this catheter and guidewire arrangement can be inserted into the venous system to obtain anatomical images of neighbouring arteries.

Using this imaging technique in conjunction with conventional MR techniques (e.g., spin relaxation, blood oxygenation shift), one may also assess properties of the MR signal in the environment immediately adjacent to the conductive length. This may include spectral measurements, or the measurement of relaxation times or chemical shifts, as is commonly known in the field. The MR signal detected in this way may also be used for other purposes, including different types of imaging techniques currently used for MR.

Applications

The MR-guided revascularization of occlusive arterial disease is one application that illustrates a use of the disclosed catheter. In this application, a guidewire is passed through an occluded artery to re-establish blood flow. While the guidewire is advanced through the lesion it may be important to ensure that the guidewire is intraluminal. This may be difficult to perform under conventional fluoroscopy guidance due to inadequate soft tissue contrast and the inability to distinguish between the lesion and vessel wall. MR is able to produce images with better soft-tissue contrast and small imaging coils may be placed at or near the distal tip of a guide catheter to produce high-resolution images depicting the occlusive material and vessel wall in front of the catheter. When combined with the disclosed catheter having a magnetic coupling component, and using the image-overlay techniques described above, the position of the guidewire may be displayed on high-resolution anatomical images to ensure that it is intraluminal. This may be enhanced by providing an imaging coil in the catheter in order to provide higher-resolution intravascular images.

In this disclosure, a short conductive length in a MR-compatible guidewire may be actively visualized through the reception of a MR signal in a magnetic coupling component on a catheter without the guidewire being connected directly to the MR scanner. Moreover, it enables visualization of the guidewire without requiring the addition of any internal structure modifications introduced for the purpose of imaging. This is different from other active guidewires and needles, for example those described in the patent literature (such as described in U.S. Pat. No. 6,675,033), which include a coaxial transmission line electrically connected to the receive chain of the MR scanner where the outer conductor has one conductor folded back at one end to form a dipole antenna.

The present disclosure may also be distinguished from other external devices that have been proposed. Hillenbrand et al. (Reference 15) have proposed the use of a bazooka balun located outside the body to visualize and suppress currents on a guidewire. This is accomplished by inductively coupling the guidewire to the balun. Because this is an external device, it is unable to visualize "MR-compatible" guidewires (e.g., guidewires having a mostly non-conductive length) because the conducting structure needs to be long enough so that it exits the patient's body.

Another device was recently proposed by Zanchi et al. (Reference 16) that has a single-loop external coil that is used to detect corrects on a guidewire. The AC signal across the coil is then optically transmitted outside the magnet room and so that the magnitude of the signal can be monitored. Again this is an external device located and cannot be used to monitor currents on MR-compatible guidewires.

REFERENCES

1. Weiss S, Kuehne T, Brinkert F, Krombach G, Katoh M, Schaeffter T, Guenther R W, Buecker A. In vivo safe catheter visualization and slice tracking using an optically detunable resonant marker. Magn Reson Med 2004; 52(4): 860-868.
2. Omary R A, Unal O, Koscielski D S, Frayne R, Korosec F R, Mistretta C A, Strother C M, Grist T M. Real-time MR imaging-guided passive catheter tracking with use of gadolinium-filled catheters. J Vasc Interv Radiol 2000; 11(8): 1079-1085.
3. Miquel M E, Hegde S, Muthurangu V, Corcoran B J, Keevil S F, Hill D L, Razavi R S. Visualization and tracking of an inflatable balloon catheter using SSFP in a flow phantom and in the heart and great vessels of patients. Magn Reson Med 2004; 51(5):988-995.
4. Kozerke S, Hegde S, Schaeffter T, Lamerichs R, Razavi R, Hill D L. Catheter tracking and visualization using 19F nuclear magnetic resonance. Magn Reson Med 2004; 52(3):693-697.
5. Dumoulin C L, Souza S P, Darrow R D. Real-time position monitoring of invasive devices using magnetic resonance. Magn Reson Med 1993; 29(3):411-415.
6. Hillenbrand C M, Elgort D R, Wong E Y, Reykowski A, Wacker F K, Lewin J S, Duerk J L. Active device tracking and high-resolution intravascular MRI using a novel catheter-based, opposed-solenoid phased array coil. Magn Reson Med 2004; 51(4):668-675.
7. Ocali O, Atalar E. Intravascular magnetic resonance imaging using a loopless catheter antenna. Magn Reson Med 1997; 37(1):112-118.
8. Liu C Y, Farahani K, Lu D S, Duckwiler G, Oppelt A. Safety of MRI-guided endovascular guidewire applications. J Magn Reson Imaging 2000; 12(1):75-78.
9. Nitz W R, Oppelt A, Renz W, Manke C, Lenhart M, Link J. On the heating of linear conductive structures as guide wires and catheters in interventional MRI. J Magn Reson Imaging 2001; 13(1):105-114.
10. Yeung C J, Atalar E. A Green's function approach to local rf heating in interventional MRI. Med Phys 2001; 28(5): 826-832.
11. Yeung C J, Atalar E. RF transmit power limit for the barewire loopless catheter antenna. J Magn Reson Imaging 2000; 12(1):86-91.
12. Krueger S, Schmitz S, Ruhl K M, Spuentrup E, Katoh M, Linssen M, Schade H, Weiss S, Buecker A. Evaluation of an MR-compatible guidewire made in a novel micro-pultrusion process. Proceedings 15th Scientific Meeting, International Society for Magnetic Resonance in Medicine 2007:291.
13. Kraemer N, Krueger S, Schmitz S, Linssen M, Schade H, Weiss S, Guenther R, Buecker A, Krombach G. Preclinical Evaluation of a Novel Fiber Compound MR Guide Wire. Proceedings 16th Scientific Meeting, International Society for Magnetic Resonance in Medicine 2008:905.
14. Ladd M E, Quick H H. Reduction of resonant RF heating in intravascular catheters using coaxial chokes. Magn Reson Med 2000; 43(4):615-619.
15. Hillenbrand C M, Reykowski E Y, Wong E Y, Rafie S, Nitz W, Duerk J L. The Bazooka Coil: A Novel Dual-Purpose Device for Active Visualization and Reduction of Cable Currents in Electrically Conductive Endovascular Instruments. Proceedings 13th Scientific Meeting, International Society for Magnetic Resonance in Medicine 2005:197.
16. Zanchi M, Venook R, Pauly J, Scott G. An Optically-Coupled System for Quantitative Monitoring of MRI-Induced RF Currents into Long Conductors. Proceedings 16th Scientific Meeting, International Society for Magnetic Resonance in Medicine 2008:897.

Although this disclosure has referred to the conductive length as being provided on a guidewire, and the magnetic coupling component as being provided in a catheter, a person skilled in the art would understand that the conductive length and magnetic coupling component may be incorporated into other devices and combinations. For example, the conductive length may be incorporated into a non-conductive needle and the magnetic coupling component may be incorporated into a sheath for the needle. All examples and embodiments provided in this disclosure are for the purpose of illustration only and are not intended to be limiting. A person skilled in the art would understand that variations and modifications are possible within the scope of this disclosure. All references mentioned are hereby incorporated by reference in their entirety.

The invention claimed is:

1. A catheter for magnetic resonance (MR) guided procedures comprising:
a catheter body having a lumen for accommodating an intravascular device removably inserted through the catheter;
a component having a portion defining at least one magnetic coupling loop in the catheter body, the component being designed to couple with a conductive length on the intravascular device via a magnetic coupling in the absence of a physical electrical connection with the intravascular device, to result in a signal detectable by a processor as a measurement signal;
the catheter having a connection to deliver the signal to the processor.

2. The catheter of claim 1 wherein the signal is further indicative of a property of the intravascular device.

3. The catheter of claim 1 wherein the signal is indicative of the position or length of the intravascular device.

4. The catheter of claim 1 wherein the signal is indicative of a surrounding environment of the intravascular device.

5. The catheter of claim 1 wherein the signal is used to produce an image of a region surrounding the intravascular device.

6. The catheter of claim 1 further comprising an intravascular imaging coil configured for acquiring intravascular imaging signals.

7. The catheter of claim 1 further comprising an electronic component for processing the signal.

8. The catheter of claim 7 wherein the electronic component is embedded in the catheter body.

9. The catheter of claim 7 wherein the electronic component is selected from the group consisting of: an amplifier circuit, a tuning circuit, a detuning circuit, a matching network, a filter circuit, an encoding circuit, and a current suppression circuit.

10. The catheter of claim 1 further comprising a safety component.

11. The catheter of claim 10 wherein the safety component is selected from the group consisting of: a RF choke and a balun.

12. The catheter of claim 1 further comprising a radiopaque marker.

13. The catheter of claim 1 wherein the component is a coil.

14. The catheter of claim 13 wherein the coil is a toroidal coil.

15. The catheter of claim 13 wherein the coil is a rectangular toroidal coil.

16. The catheter of claim 1 wherein the component has a cylindrical configuration comprising two concentric conductive tubes joined at one end of the cylindrical configuration and spaced apart by a non-conductive material.

17. The catheter of claim 1 wherein the component has a length in the range of about 0.1 mm to about 10 cm.

18. The catheter of claim 1 wherein the catheter has an outer diameter in the range of 0.3 mm to 5 cm and the component has a diameter corresponding to the catheter outer diameter.

19. The catheter of claim 1 wherein the component comprises a conductive material selected from the group consisting of: copper, aluminum, nitinol, gold, platinum, a flexible copper clad laminate, and combinations thereof.

20. The catheter of claim 1 wherein the magnetic coupling component comprises a non-conductive supportive material.

21. The catheter of claim 20 wherein the supportive material is a bio-compatible polymer.

22. The catheter of claim 21 wherein the bio-compatible polymer is selected from the group consisting of: polyetheretherketone, delrin, polyimide, polyvinylchloride, polyethylene, polycarbonate, polysulfone, polypropylene, polytetrafluoroethylene, and combinations thereof.

23. The catheter of claim 1 wherein there is a plurality of components on the catheter, wherein each component has a portion defining at least one magnetic coupling loop.

24. A combination for magnetic resonance (MR) guided procedures comprising:
the catheter of claim 1; and
an MR-compatible intravascular device designed to pass through the lumen of the catheter, the intravascular device having a conductive length;
wherein the component having a portion defining at least one magnetic coupling loop in the catheter is configured to couple with the conductive length via a magnetic coupling in the absence of a physical electrical connection with the intravascular device, to result in a signal detectable by the processor as a measurement signal.

25. The combination of claim 24 wherein the conductive length is at or near the distal tip of the intravascular device.

26. The combination of claim 24 wherein the conductive length has a length in the range of 1 cm to 30 cm.

27. The combination of claim 24 wherein the conductive length comprises conductive material selected from the group consisting of: nitinol, stainless steel, platinum, gold, and combinations thereof.

28. The combination of claim 24 wherein the intravascular device, excluding the conductive length, comprises an MR-compatible material.

29. The combination of claim 24 wherein there is a plurality of conductive lengths on the intravascular device, the conductive lengths being separated by non-conductive joints or non-conductive lengths.

30. The combination of claim 29 wherein there is a plurality of components on the catheter corresponding to the plurality of conductive lengths, wherein each component has a portion defining at least one magnetic coupling loop.

31. The combination of claim 24 wherein the intravascular device is a guidewire.

32. A method of monitoring a magnetic resonance (MR) guided procedure comprising:
providing the combination of claim 24 located in a patient, the intravascular device having been removably inserted through the catheter;
inducing a current in the conductive length;
delivering a signal to a processor, the signal resulting from magnetic coupling between the component and the conductive length, in the absence of a physical electrical connection between the component and the intravascular device, the magnetic coupling resulting in the signal detectable by the processor as a measurement signal.

33. The method of claim 32 further comprising determining the position of the intravascular device using the signal.

34. The method of claim 32 further comprising producing an image of a region surrounding the intravascular device using the signal.

35. The method of claim 32 further comprising obtaining a position image indicative of a position of the intravascular device using the signal and superimposing the position image on an anatomical image.

36. The method of claim 32 further comprising calculating a position of the intravascular device based on a signal void in an image reconstructed from the signal.

37. The method of claim 36 further comprising displaying the calculated position information on an anatomical image.

38. The method of claim 32 wherein the catheter comprises an intravascular imaging coil, the method further comprising obtaining an intravascular image using the intravascular imaging coil.

39. The method of claim 32 wherein the procedure is a revascularization procedure.

40. The combination of claim 28 wherein the MR-compatible material is selected from the group consisting of: fibreglass, graphite, carbon fibre, and a polymer.

41. The catheter of claim 1 wherein the component is configured to magnetically couple with the intravascular device while there is no physical electrical contact between the magnetic coupling component and the intravascular device.

42. The catheter of claim 1 wherein the component is conductively isolated from the lumen.

\* \* \* \* \*